United States Patent
Jacob (10) Patent No.: US 10,680,021 B2
(45) Date of Patent: Jun. 9, 2020

(54) ACTIVE PIXEL SENSOR COMPUTED TOMOGRAPHY (CT) DETECTOR AND METHOD OF READOUT

(71) Applicant: General Electric Company, Schenectady, NY (US)

(72) Inventor: Biju Jacob, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 71 days.

(21) Appl. No.: 15/593,963

(22) Filed: May 12, 2017

(65) Prior Publication Data

US 2018/0331137 A1    Nov. 15, 2018

(51) Int. Cl.
| | |
|---|---|
| H01L 27/146 | (2006.01) |
| H04N 5/378 | (2011.01) |
| H04N 5/374 | (2011.01) |
| A61B 6/03 | (2006.01) |
| A61B 6/00 | (2006.01) |
| G01T 1/24 | (2006.01) |
| H04N 5/3745 | (2011.01) |
| H04N 5/32 | (2006.01) |

(52) U.S. Cl.
CPC ........ *H01L 27/14603* (2013.01); *A61B 6/032* (2013.01); *A61B 6/4233* (2013.01); *G01T 1/247* (2013.01); *H01L 27/14663* (2013.01); *H04N 5/32* (2013.01); *H04N 5/374* (2013.01); *H04N 5/378* (2013.01); *H04N 5/37452* (2013.01)

(58) Field of Classification Search
None
See application file for complete search history.

(56) References Cited

U.S. PATENT DOCUMENTS

| | | |
|---|---|---|
| 5,323,430 A | 6/1994 | Nobuta et al. |
| 6,335,958 B1 | 1/2002 | Munier et al. |
| 7,095,028 B2 | 8/2006 | Mollov et al. |
| 8,546,859 B2 | 10/2013 | Maes et al. |
| 8,847,169 B2 | 9/2014 | Yuan et al. |
| 2007/0001119 A1 | 1/2007 | Mollov et al. |
| 2007/0075252 A1 | 4/2007 | Misawa |
| 2007/0104311 A1 | 5/2007 | Possin et al. |
| 2008/0165921 A1 | 7/2008 | Tkaczyk et al. |
| 2010/0243892 A1* | 9/2010 | Dupont ................... G01J 5/02 250/332 |

(Continued)

FOREIGN PATENT DOCUMENTS

| | | |
|---|---|---|
| DE | 102012202500 A1 | 8/2013 |
| WO | 9931874 A1 | 6/1999 |

OTHER PUBLICATIONS

Hsieh et al., "Dual-energy X-ray CT with Fast-kVp Switch", GE Healthcare Technologies.

(Continued)

*Primary Examiner* — Edwin C Gunberg
(74) *Attorney, Agent, or Firm* — Fletcher Yoder, P.C.

(57) ABSTRACT

The present approach relates to implementations of a CT detector integrating CT scintillator packs on a fast, low electronic noise and scalable CMOS active pixel sensor substrate. In one embodiment, a large 3-side buttable CMOS active pixel array with built-in column analog-to-digital conversion (ADC) circuitry (e.g., ASICs) integrated onto the same wafer is used.

14 Claims, 6 Drawing Sheets

(56) References Cited

U.S. PATENT DOCUMENTS

| | | | |
|---|---|---|---|
| 2013/0003928 A1* | 1/2013 | Pietig | G01T 1/17 |
| | | | 378/62 |
| 2014/0301534 A1 | 10/2014 | Rao et al. | |
| 2015/0162373 A1* | 6/2015 | Kim | H01L 31/02322 |
| | | | 257/13 |
| 2016/0373672 A1* | 12/2016 | Liu | H04N 5/3575 |
| 2017/0195607 A1* | 7/2017 | Bulteel | H04N 5/378 |

OTHER PUBLICATIONS

Vogtmeier et al., "CMOS Compatible Through Wafer Interconnects for Medical Imaging Detectors", IEEE Nuclear Science Symposium Conference Record, NSS '07, Oct. 26-Nov. 3, 2007.

Theuwissen, "CMOS image sensors: State-of-the-art", Solid-State Electronics, vol. 52, pp. 1401-1406, 2008.

Farrier et al., "Very Large Area CMOS Active-Pixel Sensor for Digital Radiography", IEEE Transactions on Electron Devices, vol. 56, No. 11, Nov. 2009.

Spahn, "X-Ray Detectors in Healthcare and Their Applications", Siemens AG Healthcare, Sep. 4, 2012.

Konstantinidis et al., "The Dexela 2923 CMOS X-ray detector: A Flat Panel Detector Based on CMOS Active Pixel Sensors for Medical Imaging Applications", Nuclear Instruments and Methods in Physics Research, vol. 689, pp. 12-21, Oct. 11, 2012.

Bain, "Imaging Sensor (3 Side Buttable)", STFC Innovations, 2015.

Application No. PCT/US2018/031384; International Search Report and Written Opinion dated Nov. 15, 2018; p. 1-12.

* cited by examiner

ACTIVE PIXEL SENSOR COMPUTED TOMOGRAPHY (CT) DETECTOR AND METHOD OF READOUT

TECHNICAL FIELD

The subject matter disclosed herein relates to the fabrication and use of radiation detectors, including X-ray radiation detectors fabricated using pixels arrays having integrated readout electronics.

BACKGROUND

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject.

By way of example, computed tomography (CT) imaging systems are used to generate images in a non-invasive manner by acquiring X-ray transmission data over a range of angular views about a patient and reconstructing the measured data to generate volumetric or cross-sectional views of the patient. Such computed tomography approaches may be used for medical imaging, as well as for certain industrial or security screening applications.

In CT, a portion of the radiation passes through the subject or object and impacts a detector, where representative signals are acquired. To acquire data over a useful angular range, data is acquired nearly continuously by the detector over the course of an examination, in contrast to conventional radiography, where the detector only acquired data at discrete acquisitions or shots. As a result, certain requirements are placed on a CT detector that are not necessary for other detectors where less continuous types of data collection occur. In particular, to facilitate rapid readout, each pixel of the detector typically has its own readout channel, resulting in a massively parallel readout architecture. Such architectures, however, may impose their own corresponding issues, such as noise associated with the distance the analog signals must travel prior to digitization and, in arrangements where the digital conversion circuitry is placed near to the photodiode structures generating the signals, the heat from these circuits may degrade the performance of the detection circuitry.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a detector module configured for use in a computed tomography (CT) detector is provided. In accordance with this implementation, the detector module includes an array of pixels formed on a substrate, each pixel comprising an array of sub-pixels. The detector module further includes readout circuitry integrated on one end of the substrate such that three remaining edges of the substrate are configured to abut corresponding edges of other detector modules. The readout circuitry for each column of pixels comprises multiple readout channels for that column, each readout channel configured to sequentially read out multiple pixels within the respective column.

In a further implementation, a detector module configured for use in a computed tomography (CT) detector is provided. In accordance with this implementation, the detector module includes a plurality of columns of pixels formed on a substrate, wherein pixels within each column are grouped into blocks of two or more pixels. The detector module further includes readout circuitry formed integrally on a substrate. The readout circuitry comprises a separate readout channel for each block of pixels in each column such that the number of readout channels for each column corresponds to the number of blocks of pixels in each column.

In an additional embodiment, a method for reading out a computed tomography (CT) detector is provided. In accordance with this method, for each column of pixels within an array of pixels, blocks of pixels within a respective column are read out using a different analog-to-digital (ADC) conversion readout channel for each block. The ADC readout channels for block of pixels is formed on the same substrate as the array of pixels.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific implementations will be described below. In an effort to provide a concise description of these implementations, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While the following discussion is generally provided in the context of medical imaging, it should be appreciated that the present techniques are not limited to such medical contexts. Indeed, any examples and explanations provided in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

The present approaches relate to the fabrication of a radiation detector for use in a computed tomography (CT) imaging system using multiple tiled detector panels. In particular, the present approach employs a matrix readout of pixel arrays formed on the panels where a set of pixels is multiplexed to a readout channel. This is in contrast to conventional approaches, where each pixel is physically connected to a dedicated readout channel. In one embodiment of the present approach, a three-side buttable CMOS (Complementary Metal Oxide Semiconductor) active pixel array (i.e., the pixel array is configured to abut other pixel arrays on three-sides) with column analog-to-digital conversion (ADC) circuitry integrated onto the same wafer on which the photodiode array is formed is used. As used herein an "active pixel" has an amplifier formed within each pixel circuit, such that an amplified analog signal is read out from each pixel. As noted above, digital conversion may be performed by an integrated ADC associated with each column, or with subsets of each column, of pixels. The proposed architecture allows the X-ray detector to operate at frame rates of greater than the 10 kHz needed to support fast CT applications. This is enabled by the active pixel sensor with global shutter capability implemented on a 3-side buttable CMOS imager architecture as noted above. As discussed herein, also contemplated is a platform concept for the detector that is scalable across the CT product portfolio with different coverage requirements.

In addition, a further benefit of the architecture discussed herein is improved thermal performance. In particular, the proposed 3-side buttable architecture simplifies the thermal issues by moving the heat sources (e.g., ASIC readout circuitry) away from sensitive elements of the detector, such as the photodiodes and scintillator, whose performance may vary in the presence of temperature variation.

Figure 1:
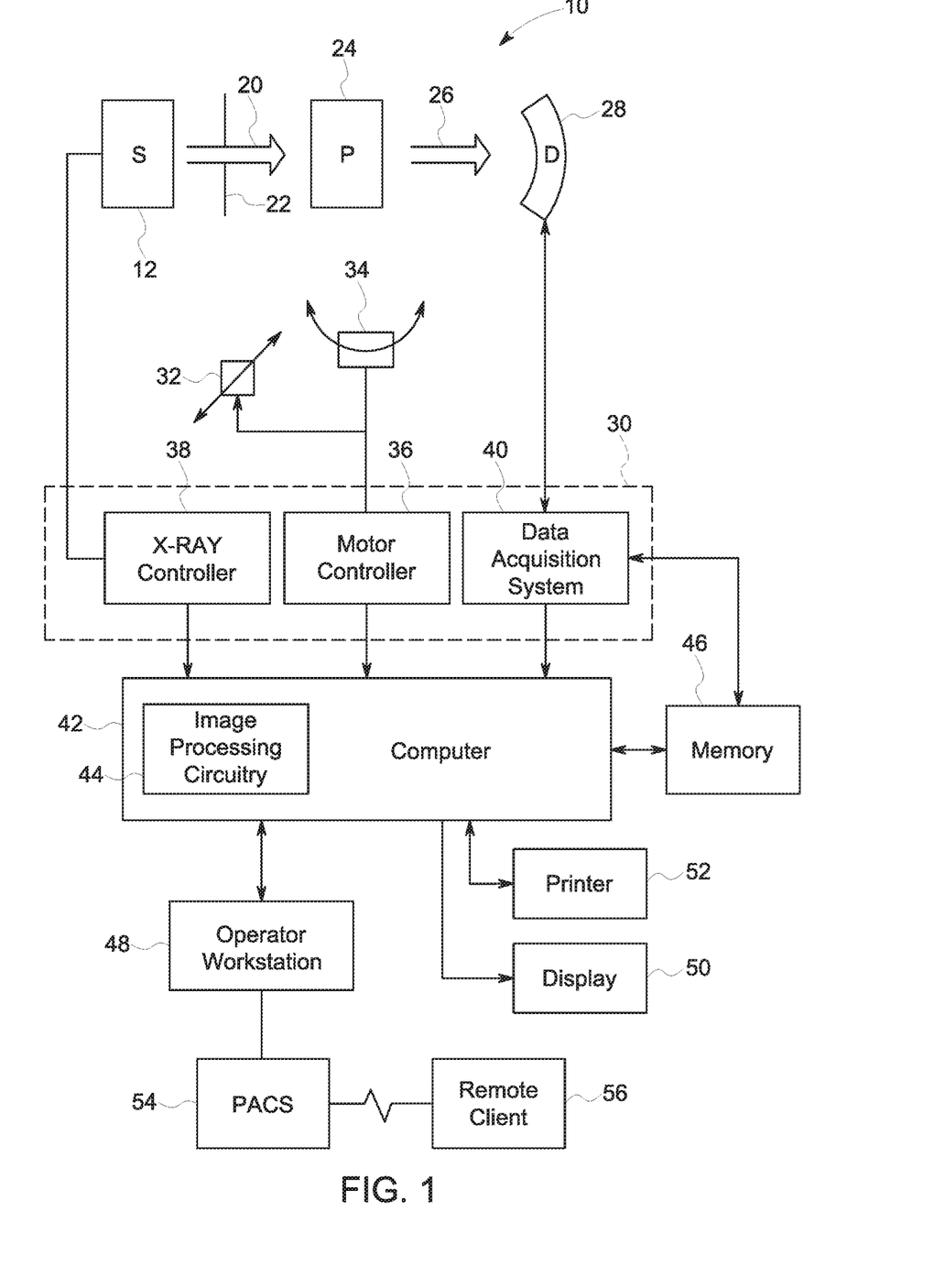
FIG. 1 is a schematic illustration of an embodiment of a Computed Tomography (CT) system in accordance with aspects of the present disclosure.

With the preceding discussion in mind, FIG. 1 illustrates an embodiment of an imaging system 10 for acquiring and processing image data in accordance with aspects of the present disclosure. In the illustrated embodiment, system 10 is a Computed Tomography (CT) system designed to acquire X-ray projection data, to reconstruct the projection data into a tomographic image, and to process the image data for display and analysis. The depicted CT imaging system 10 includes an X-ray source 12. As discussed in detail herein, the source 12 may include one or more X-ray sources, such as an X-ray tube or one or more enclosures containing solid state emission structures. The X-ray source 12, in accordance with certain contemplated embodiments, is configured to emit an X-ray beam 20 from one or more emission spots (e.g., focal spots), which may correspond to X-ray emission regions on a target structure (e.g., an anode structure) impacted by a directed electron beam.

In certain implementations, the source 12 may be positioned proximate to a filter assembly or beam shaper 22 that may be used to steer the X-ray beam 20, to define the shape and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-rays 20, resulting in attenuated X-rays 26 that impact a detector array 28 formed from an number of the detector modules or panels (e.g., a tiled array of such panels or modules) as discussed herein. Each detector module has a plurality of detector elements (e.g., pixels) as discussed below. Each detector element produces an electrical signal that represents the intensity of the X-ray beam incident at the position of the detector element when the beam strikes the detector 28. Electrical signals are acquired and processed to generate one or more scan datasets. In implementations discussed herein, the detector 28 includes integrated readout circuitry and control logic, allowing the output of digitized signals to downstream components. In the depicted example, the detector 28 is coupled to the system controller 30, which commands acquisition of the digital signals generated by the detector 28.

A system controller 30 commands operation of the imaging system 10 to execute filtration, examination and/or calibration protocols, and to process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the photodetector to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
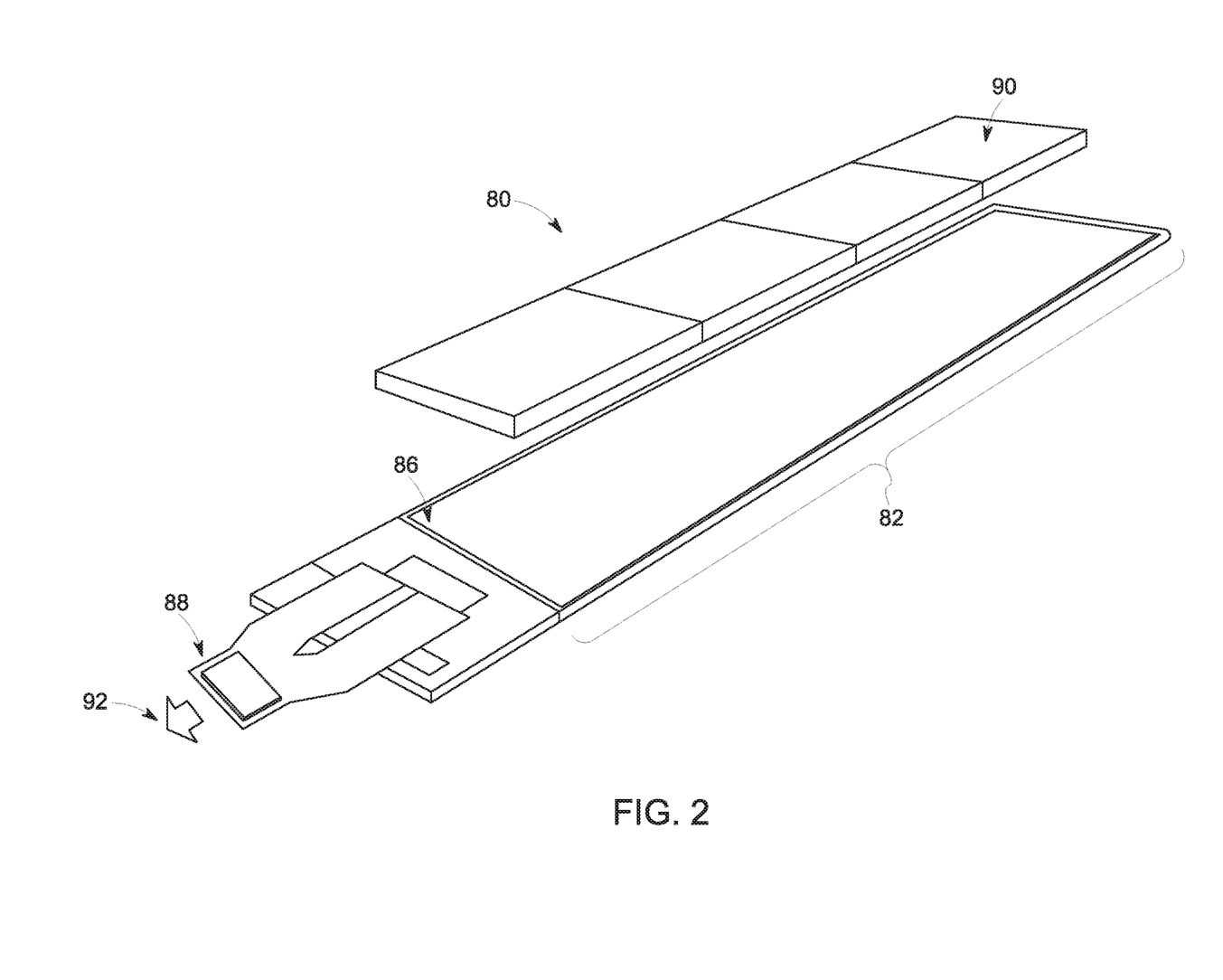
FIG. 2 depicts an exploded view of a detector panel and scintillator pack in accordance with aspects of the present disclosure.

With the preceding discussion of an overall imaging system 10 in mind, FIG. 2 depicts a detector panel 80 having an array of pixels that may be used in combination with other such detector panels 80 to form the overall detector 28. By way of example, the depicted panel 80 may constitute the base tilable, independent sub-unit of a detector assembly. For example, some number of detector panels 80 may be arranged, such as linearly arranged, into a higher level assembly unit, such as a detector module. Detector modules themselves may then be arranged to form the overall detector 28 of the CT imager.

In the depicted example, the detector panel 80 consists of an active pixel array 82, which as noted above is indicative of an amplifier circuit being present within the pixel circuitry. In one such example the readout and/or digitization circuitry is formed on the same contiguous wafer as the pixel array, with data transmission occurring along data lines formed on the wafer itself, as opposed to separately connected interconnect structures. In the depicted example, the integrated ASIC 86 is at one end of the active pixel array 82. The depicted arrangement of positioning the readout circuitry 86 at the periphery of the pixel matrix 82 (i.e., outside the X-ray field-of-view) keeps the sensitive pixel circuitry and scintillator material 90 (discussed below) away from the heat generated by the readout circuitry 86, thereby improving thermal performance. This may be contrasted with conventional arrangements, in which the scintillator, photodiode array, and ASICs are formed as a vertical stack (such as may be suitable to a massively parallel readout operation where each pixel has a dedicated readout channel), which may subject the sensitive pixel circuitry and scintillator material to the heat generated by the ASICs during operation.

The active pixel sensor array 82 may be suitably scaled based on the detector configuration. For example, a 150 mm long active pixel sensor array 82 may be formed from an 8 inch c-Si wafer, i.e., an 8 inch CMOS wafer. Larger panels, such as ~200 mm arrays 82 may be formed from larger diameter c-Si wafers.

In addition, a scintillator pack 90 is pictured in FIG. 2. The scintillator pack 90, in operation, is positioned proximate to the active surface of the active pixel sensor array 82 and, in response to X-ray photons, emits lower energy photons, such as photons in an optical energy range or other energy range suitable for detection by photodetectors. The photodiodes of the active pixel array 82 then detect the optical (or other non-X-ray) photons emitted by the scintillator pack 90 to generate the charges read out by the readout electronics 86.

In electronic communication with the readout electronics (i.e., ASIC 86) is a data output connector 88, here depicted as a flexible circuit connector, that may be used to connect the detector module 80 into a provided connector structure in communication with the data acquisition circuitry and/or controllers. Data 92 acquired by the detector module 80 is thus communicated to downstream circuitry via the output connector 88

As previously noted, the depicted detector panel 80 arrangement is a structure that may be three-side buttable. That is, the depicted detector panel 80 may abut other, comparable detector panels 80 on every side except the side having the data output connector 88. This feature allows detectors to be built with wide coverage (e.g., ~160 mm).

Figure 3:
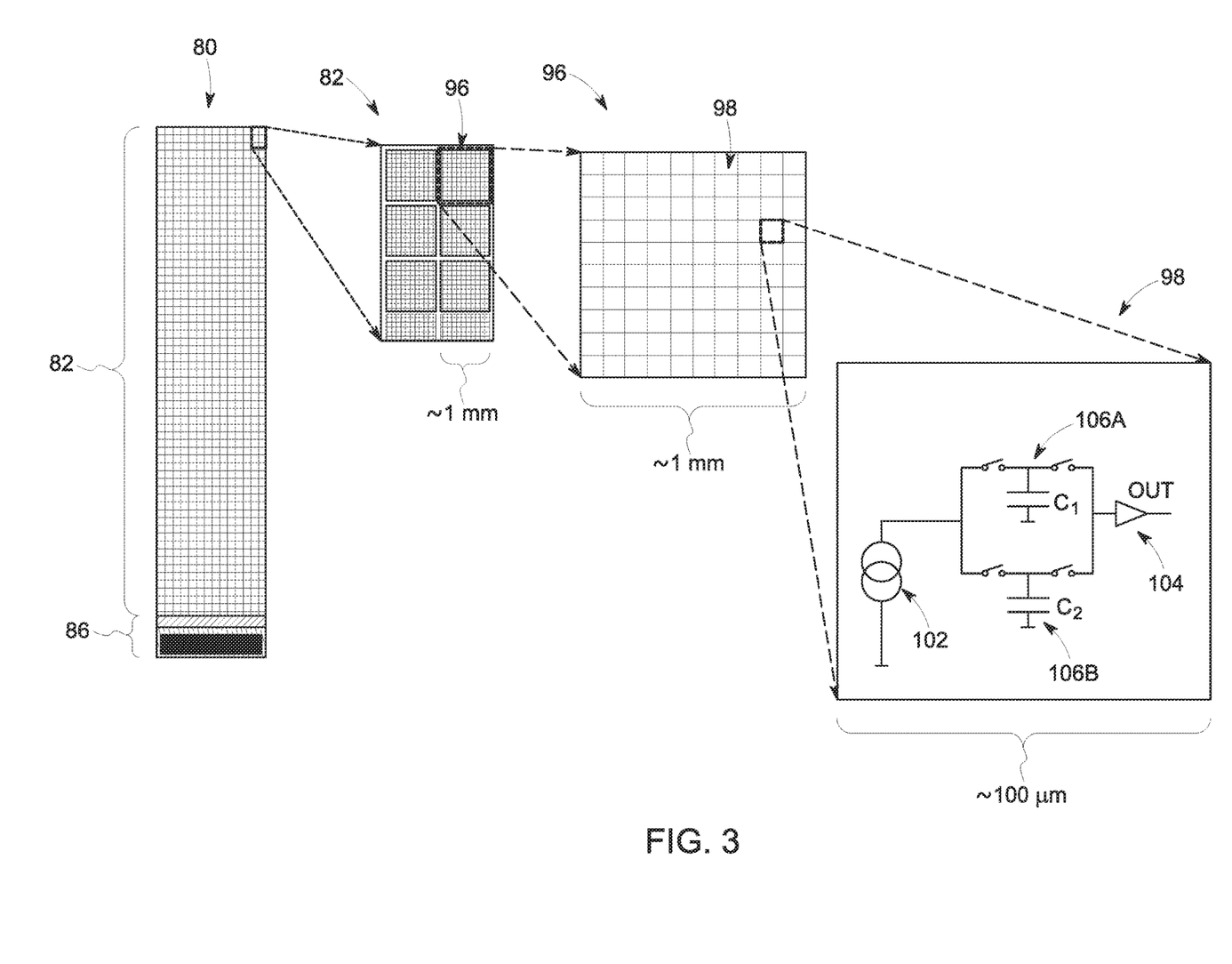
FIG. 3 depicts a progressively zoomed view of features of a detector panel in accordance with aspects of the present disclosure.

Turning to FIG. 3, the active matrix architecture is illustrated in greater detail by progressively zooming in on features of the architecture proceeding from left to right in the drawing. Thus, the rightmost level of abstraction illustrates the active pixel array 82 and integrated readout circuitry 86 of a detector panel 80. In the depicted example, the portion of the active pixel array 82 corresponding to the pixel electronics is a 32×128 array of pixels 96 (i.e., 32 pixels wide and 128 pixels long). As will be appreciated, other pixel array dimensions may be employed, with the present example merely being provided for illustration and to provide a real-world example. The remainder of the length of the panel 80 includes the integrated readout electronics 86. As noted above, the pixel array 82 may be abutted with other pixel arrays 82 on each side but the side having the readout electronics 86.

Progressively moving rightward in FIG. 3, a region of the active pixel array 82 is shown with the pixels 96 presented in greater detail. In the depicted example, the pixels 96 are approximately 1 mm×1 mm. Proceeding rightward in the figure, a single pixel 96, approximately 1 mm on each side, is illustrated. In this example, and as discussed in greater detail below, each pixel 96 in one implementation is comprised of an array of sub-pixels 98.

In a typical CT detector, the scintillator is pixelated and the inter-pixel gap is filled with optically reflective material to improve the light output. The image sensor array is designed to match the scintillator pixellation geometry so that perfect overlap of the scintillator pixel and the photo sensor is achieved. The inter pixel gap is of the order of 100 μm in typical CT detectors.

With this in mind, in present implementations, each pixel 96 comprises an array of sub-pixels 98, such as a 10×10 array of sub-pixels 98 having a 100 μm pitch. This structure differs from what is conventionally seen in a CT detector. In the rightmost aspect of FIG. 3, a circuitry schematic of a sub-pixel 98 in accordance with one such implementation is shown. In this example, the photo sensitive element is a photodiode 102 that generates a photocurrent current proportional to the X-ray photon energy absorbed in the scintillator pixel above it. Each sub-pixel has a built-in amplifier 104 that improves the signal-to-noise ratio. Unlike a conventional image sensor pixel, there is more than one charge storage element (e.g., capacitors 106A and 106B) in one implementation. This additional storage and the associated integrated readout electronics enable readout of the pixel 96 during an X-ray image data acquisition. This in turn enables global shutter operation and ultra-fast frame rate (e.g., >10 kHz) that facilitates certain CT acquisition modes (e.g. ultra-fast kV switching in dual energy imaging). The implementation of the charge storage elements 106 is also relevant to CT applications which benefit from highly linear signal response. The combination of a pinned photodiode 102 (which carries negligible capacitance) with a linear metal-insulator-metal (MIM) capacitor is one suitable design option. In particular, using a pinned photodiode as the photodiode 102 provides benefits in terms of linearity of the pixel response as well as improving the radiation hardness of the pixel 96.

Figure 4:
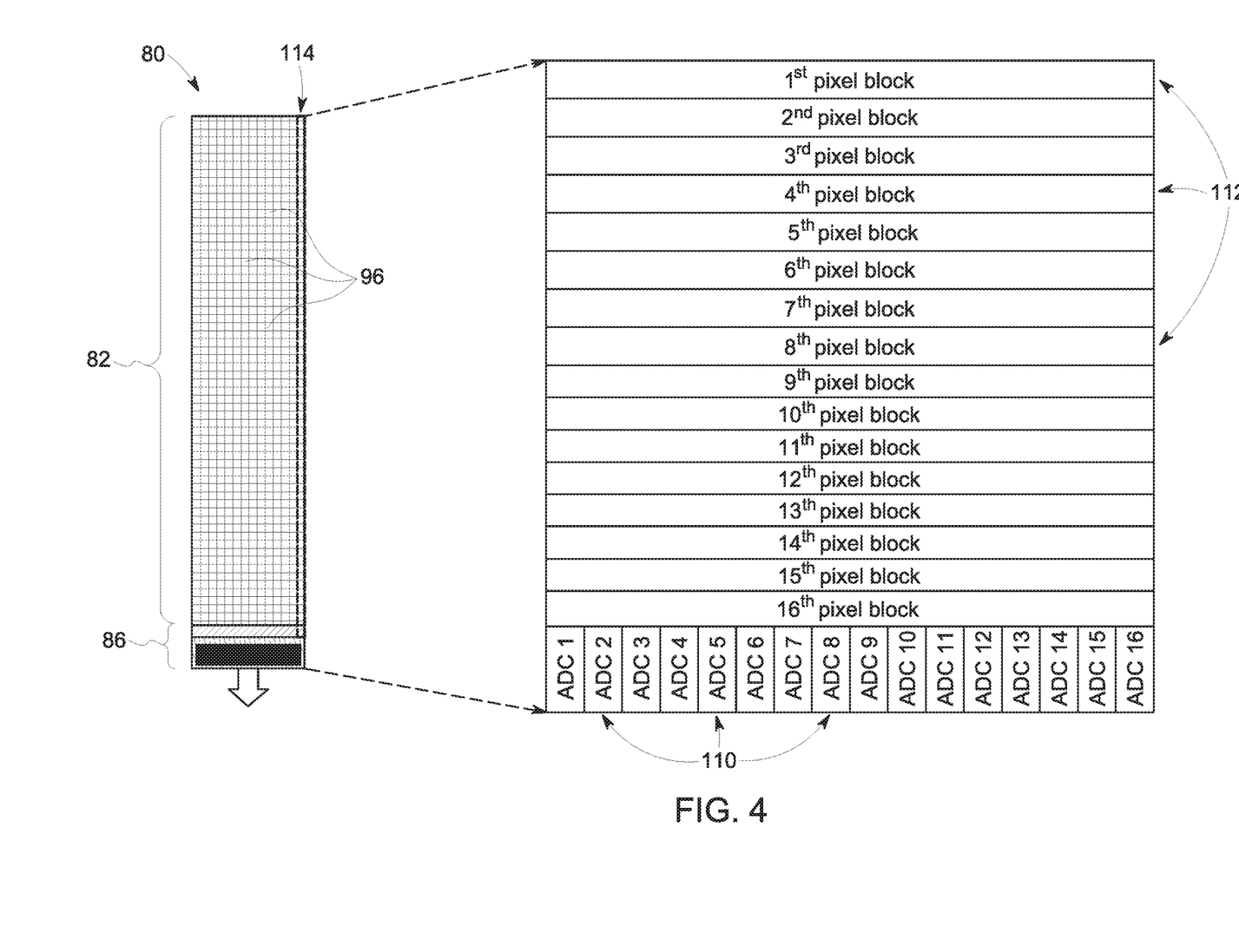
FIG. 4 depicts features block-based readout features of a detector panel in accordance with aspects of the present disclosure.

With the benefits of fast signal readout, as described above in mind, and turning to FIG. 4, a readout architecture suitable for use with the present active pixel array 82 is described. Conventional detector designs attempt to provide fast readout by employing massively parallel readout architecture (e.g., dedicated channel per photodiode). In contrast, the presently described approach employs several analog-to-digital conversion (ADC) readout channels per pixel column of the active pixel array 82. For instance, with reference to the example of FIG. 4, in this example sixteen ADCs, 110 each with approximate width of ~60 μm are positioned within a column width of 1 mm (denoted as column 114). Each ADC 110 is designed to serve a block 112 of eight pixels 96. With a line time of 10 μs, the depicted configuration enables view rates of 12.5 kHz. Signals from sub-pixels within pixels may be integrated within the pixels for readout at the pixel level, thus avoiding the need to address sub-pixels individually. In other configurations, more ADCs can be provided per pixel to enable higher view rates. Thus, each column 114 of pixels 96 is broken into blocks 112 (here blocks of eight pixels 96), with each block being readout by its own ADC 110. Thus, in this example, with respect to routing, each ADC 119 serves approximately eight pixels 96 (i.e., a block 112 of pixels), with 16 data lines per pixel and an ADC layout of 60 μm×3 mm. In terms of readout speed for this example, line time is approximately 10 μs, read time is the number of pixels per block (e.g., eight) multiplied by the line time (e.g., approximately 10 μs), so 80 μs in this example. Views per second, in this example, is 12,500 Hz.

Figure 5:
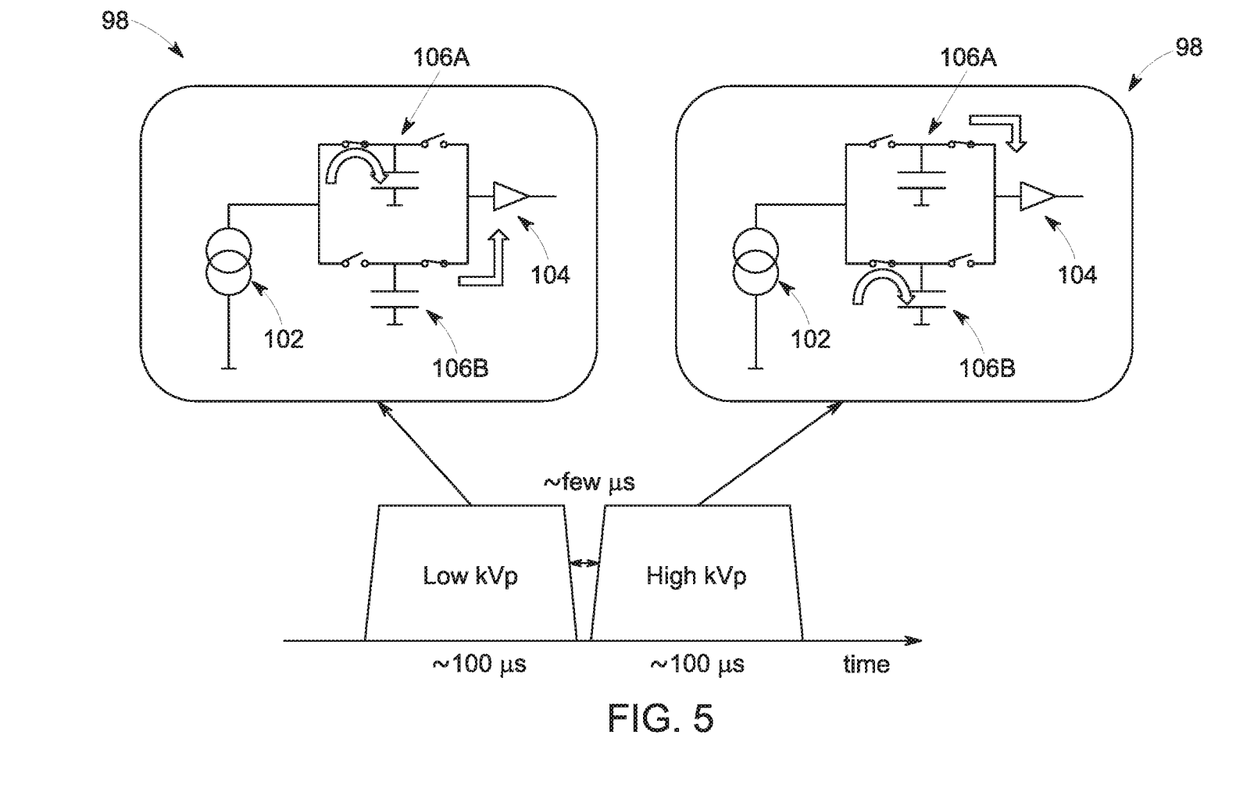
FIG. 5 depicts circuitry and charge flows of pixel circuitry during a duel-energy image acquisition in accordance with aspects of the present disclosure.

With respect to the present design approach, several benefits are achieved. For example, as noted above, dual energy imaging approaches may switch an X-ray source between two kVps (e.g., between low- and high-energy) during a scan. During a CT acquisition, fast kV switching benefits from an identical integration (i.e., time) window for all pixels 96. From the perspective of the design of the image sensor, this equates to a true global shutter operation (i.e., as opposed to continuous sequential readout). An example of one implementation of a global shutter pixel in the context of the present detector panel architecture is shown in FIG. 5.

In this example, it can be seen that capacitor 106A is used to store charge generated during a low-energy exposure. Concurrent with the low-energy exposure charge being stored in capacitor 106A, capacitor 106B, presumably storing charge accumulated during the preceding high-energy exposure, is read out and reset. Conversely, during the following high-energy exposure, capacitor 106B is used to store charge generated during the high-energy exposure and capacitor 106A, storing charge accumulated during the preceding low-energy exposure, is read out and reset. Thus, the present architecture enables the imager to acquire a new view/image during readout of the previous view.

In addition, a further benefit of the presently contemplated detector architecture is improvement of electronic noise entitlement, i.e., the theoretical limit in terms of noise performance. Various design options may be employed to reduce noise. Examples of techniques that may be employed include, but are not limited to, active reset, in-pixel correlated double-sampling, and so forth.

One example of a low-noise design is as follows: for a front lit diode, a charge per view of approximately 50 pC, a sub-pixel design as described above (e.g., one pixel 96=10× 10 μm sub-pixels 98, and a full well capacity (FWC) per pixel of 3 Me$^-$. With this design in mind, a readout method may be to connect the sub-pixels 98 in parallel during exposure, to disconnect the sub-pixels 98 after exposure, and to subsequently readout from the center pixel, thus effectively integrating the sub-pixel signals within the respective pixels to allow readout at the pixel level and avoiding the need to address sub-pixels individually. In such a context, readout noise may consist of kTC (essentially thermal noise on the capacitors 106) and analog read noise. kTC may be approximately 2,190 e$^-$ (C=30 pF) and analog read noise may be approximately 3,000×0.22=660 e$^-$, yielding a total read noise of 2,290 e$^-$. This estimate is comparable to the noise levels of current state of the art CT detectors.

Figure 6:
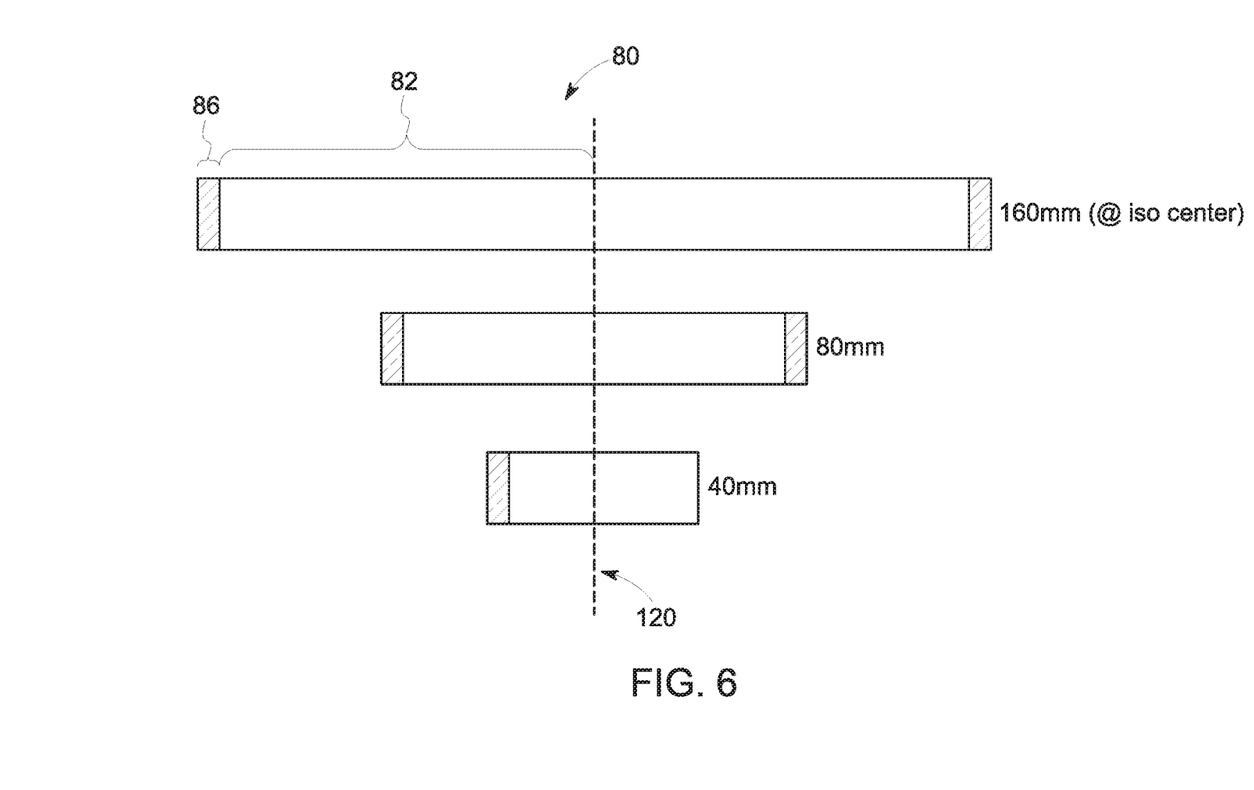
FIG. 6 illustrated scalability of the detector panels of the present approach in accordance with aspects of the present disclosure.

As noted above, another benefit of the present approach is scalability. Turning to FIG. 6, three examples are depicted demonstrating the scalability of the present approach. A typical CT product portfolio has different tiers of CT systems with varying spatial coverage (e.g., iso center coverage from 40 mm to 160 mm), performance and cost. An important factor for a cost effective detector 28 is that the design is scalable across such a product portfolio. This translates to a platform technology that can leverage volume and cost.

With the proposed 3-side buttable active matrix architecture one can build systems with a wide/varying coverage, as seen in FIG. 6. For example, in the topmost example, two 80 mm long detector panels 80 are shown abutted at their ends opposite the readout connector to provide 160 mm coverage at iso center 120. Similarly, for a detector having less coverage at isocenter 120, shown in the middle example, two 40 mm long detector panels 80 can be abutted to give 80 mm coverage at iso center 120. Where even less coverage is needed, a single detector panel 80, such as a 40 mm long detector panel 80, can be centered at iso center 120 to give 40 mm of coverage.

The integration of CT scintillator packs on a fast, low electronic noise and scalable active pixel sensor brings the best of CT and flat-panel x-ray technologies to build a high-performance detector. This is in contrast to the cone beam CT approach which employs a standard x-ray flat panel detector, where the poor detection efficiency of the x-ray scintillator and slow readout speed of the flat-panel result in an inferior detector performance.

Technical effects of the invention includes a matrix readout of the pixel array where a block of pixels is multiplexed to a readout channel. In one embodiment, a large 3-side buttable CMOS active pixel array with built-in column ADCs integrated onto the same wafer is used. In further aspects, multiple ADC readout channels are provided per pixel column to facilitate the multiplexed read out of a detector panels. In one embodiment, each image sensor pixel comprises a sub-pixel array.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A detector module for use in a computed tomography (CT) detector, the detector module comprising:
    an array of pixels formed on a substrate, each pixel comprising an array of sub-pixels;
    readout circuitry integrated on one end of the substrate such that three remaining edges of the substrate are configured to abut corresponding edges of other detector modules, wherein the readout circuitry for each column of pixels comprises multiple readout channels for that column, each column of pixels comprises a plurality of blocks of pixels, each readout channel is solely associated with a respective block of pixels of the plurality of block of pixels, the multiple readout channels are configured to be sequentially read out so that when each readout channel is read out multiple pixels within the respective block of pixels are read out simultaneously, wherein each sub-pixel within a column of pixels has a dedicated data line attached to a column amplifier and analog-to-digital converter (ADC).

2. The detector module of claim 1, wherein the readout channel for a given column of pixels comprises the respective amplifiers and ADCs of the columns of pixels.

3. The detector module of claim 1, wherein each sub-pixel comprises at least two charge storage elements.

4. The detector module of claim 1, wherein the charge storage elements of each sub-pixel are configured to operate in alternation or sequence such that, for a given sub-pixel, a first charge storage element is read-out while a second charge storage element accumulates charge.

5. The detector module of claim 1, wherein the substrate is a panel formed from a single silicon wafer such that the array of pixels and the readout circuitry are formed on the same silicon wafer.

6. The detector module of claim 1, wherein each sub-pixel comprises a pinned photodiode.

7. The detector module of claim 1, wherein each capacitor comprises a metal-insulator-metal capacitor.

8. A detector module, configured for use in a computed tomography (CT) detector, the detector module comprising:
    a plurality of columns of pixels formed on a substrate, wherein pixels within each column are grouped into blocks of two or more pixels, and each column of pixels comprises a plurality of blocks of pixels;
    readout circuitry formed integrally on a substrate, wherein the readout circuitry comprises a separate readout channel for each block of pixels in each column such that the number of readout channels for each column corresponds to the number of blocks of pixels in each column, and wherein each pixel comprises an array of sub-pixels, and wherein when each separate readout channel is sequentially read out the two or more pixels within a respective block of pixels are read out simultaneously.

9. The detector module of claim 8, wherein each sub-pixel comprises at least two capacitors as charge storage elements, and wherein the charge storage elements of each sub-pixel are configured to operate in alternation or sequence such that, for a given sub-pixel, a first charge storage element is read-out while a second charge storage element accumulates charge.

10. The detector module of claim 8, wherein each sub-pixel comprises a pinned photodiode.

11. The detector module of claim 8 wherein each readout channel comprises analog-to-digital conversion (ADC) circuitry such that each block of pixels within a column has a separate ADC circuit.

12. The detector module of claim 8, wherein the substrate is a panel formed form a single c-Si wafer such that the columns of pixels and the readout circuitry are formed on the same c-Si wafer.

13. A method for reading out a computed tomography (CT) detector, comprising:
    for each column of pixels within an array of pixels, reading out blocks of pixels within a respective column using a different analog-to-digital (ADC) conversion readout channel for each block;
    wherein the ADC readout channels for block of pixels is formed on the same substrate as the array of pixels, and wherein each pixel comprises an array of sub-pixels, each block of pixels comprises two or more pixels, and each column of pixels comprises a plurality of blocks of pixels, and wherein when each ADC readout channel is sequentially read out the two or more pixels within a respective block of pixels are read out simultaneously.

14. The method of claim 13, wherein each sub-pixel comprises two or more charge capacitors as storage elements, and wherein the charge storage elements of each sub-pixel are read out in alternation or sequence such that, for a given sub-pixel, a first charge storage element is read-out while a second charge storage element accumulates charge.

* * * * *